(12) United States Patent
Franceschina et al.

(10) Patent No.: US 11,896,841 B2
(45) Date of Patent: Feb. 13, 2024

(54) PHOTO-THERMAL TARGETED TREATMENT SYSTEM WITH INTEGRATED PRE-CONDITIONING, AND AUTOMATIC TRIGGERING OF PHOTO-THERMAL TARGETED TREATMENT VIA MEASUREMENT OF SKIN SURFACE TEMPERATURE AND ASSOCIATED METHODS

(71) Applicant: QUANTA SYSTEM S.P.A., Samarate (IT)

(72) Inventors: Cesare Plinio Franceschina, Valdidentro (IT); Marco Tagliaferri, Taino (IT); Emil A. Tanghetti, Sacramento, CA (US); Fabio Cannone, Melzo Milan (IT)

(73) Assignee: QUANTA SYSTEM S.P.A., Samarate (IT)

( * ) Notice: Subject to any disclaimer, the term of this patent is extended or adjusted under 35 U.S.C. 154(b) by 54 days.

(21) Appl. No.: 16/972,711

(22) PCT Filed: Jun. 10, 2019

(86) PCT No.: PCT/IB2019/000793
§ 371 (c)(1),
(2) Date: Dec. 7, 2020

(87) PCT Pub. No.: WO2019/234507
PCT Pub. Date: Dec. 12, 2019

(65) Prior Publication Data
US 2021/0259770 A1 Aug. 26, 2021

Related U.S. Application Data

(60) Provisional application No. 62/745,720, filed on Oct. 15, 2018, provisional application No. 62/682,597, filed on Jun. 8, 2018.

(51) Int. Cl.
*A61B 18/20* (2006.01)
*A61N 5/06* (2006.01)
(Continued)

(52) U.S. Cl.
CPC .......... *A61N 5/0613* (2013.01); *A61B 18/203* (2013.01); *A61B 2017/0019* (2013.01);
(Continued)

(58) Field of Classification Search
CPC . A61B 18/18; A61B 2018/1807; A61B 18/20; A61B 18/203; A61B 2018/20351;
(Continued)

(56) References Cited

U.S. PATENT DOCUMENTS 5,810,801 A     9/1998   Anderson et al.
5,968,034 A * 10/1999   Fullmer ............... A61B 18/203
                                                                  606/9

(Continued)

FOREIGN PATENT DOCUMENTS

RU            55292 U1     8/2006
RU         120008 U1     9/2012
(Continued)

*Primary Examiner* — Ahmed M Farah
(74) *Attorney, Agent, or Firm* — Dickinson Wright PLLC; Andrew D. Dorisio (57) ABSTRACT

A photo-thermal targeted treatment system for damaging a target embedded in a medium includes a controller and a photo-thermal treatment unit including a light source. The controller is configured for administering a treatment protocol using the light source at a preset power setting and a preset pulse timing setting. Also, a method for automatically initiating a treatment protocol using a photo-thermal targeted treatment system includes administering a cooling mechanism at a treatment location, monitoring a skin surface temperature at the treatment location and, when the skin surface temperature reaches a preset threshold, automati- (Continued)

cally initiating the photo-thermal treatment protocol. Further, a method for automatically terminating a treatment protocol using includes, during administration of the treatment protocol at a treatment area, monitoring a skin surface temperature at the treatment location, and when the skin surface temperature reaches a preset threshold, automatically terminating the treatment protocol.

21 Claims, 7 Drawing Sheets

(51) Int. Cl.
*A61B 18/00* (2006.01)
*A61N 5/00* (2006.01)
*A61N 5/067* (2006.01)
*A61B 17/00* (2006.01)

(52) U.S. Cl.
CPC .............. *A61B 2017/00172* (2013.01); *A61B 2018/00005* (2013.01); *A61B 2018/00452* (2013.01); *A61B 2018/00458* (2013.01); *A61B 2018/00708* (2013.01); *A61B 2018/00761* (2013.01); *A61B 2018/00791* (2013.01); *A61B 2018/20351* (2017.05); *A61N 5/067* (2021.08); *A61N 2005/002* (2013.01); *A61N 2005/0626* (2013.01); *A61N 2005/0651* (2013.01); *A61N 2005/0659* (2013.01)

(58) Field of Classification Search
CPC ......... A61B 2018/205547; A61B 2018/00005; A61B 2018/00452; A61B 2018/00458; A61B 2018/0047; A61B 2018/00476; A61B 2018/00636; A61B 2018/00642; A61B 2018/00666; A61B 2018/00702; A61B 2018/00732; A61B 2018/00761; A61B 2018/00791; A61N 5/06; A61N 5/0613; A61N 5/0616; A61N 5/0617; A61N 2005/0626; A61N 2005/0643; A61N 2005/065; A61N 2005/0659; A61N 2005/067
USPC .... 606/9–12, 20, 22, 23, 26; 607/88–91, 96, 607/100, 108; 128/898
See application file for complete search history.

(56) References Cited

U.S. PATENT DOCUMENTS

| | | | | |
|---|---|---|---|---|
| 6,171,301 | B1* | 1/2001 | Nelson | A61N 5/062 606/9 |
| 6,997,923 | B2* | 2/2006 | Anderson | A61N 7/02 606/17 |
| RE42,594 | E* | 8/2011 | Tankovich | A61B 18/203 606/9 |
| 8,029,501 | B2* | 10/2011 | Miller | A61B 18/20 606/9 |
| 8,556,887 | B2* | 10/2013 | Cornil | A61N 5/0616 606/9 |
| 9,028,469 | B2* | 5/2015 | Jones | A61B 18/203 606/2 |
| 2004/0005349 | A1 | 1/2004 | Neev | |
| 2005/0049582 | A1* | 3/2005 | DeBenedictis | A61B 18/20 606/9 |
| 2005/0107852 | A1 | 5/2005 | Levernier et al. | |
| 2005/0137658 | A1 | 6/2005 | Hennings | |
| 2005/0251118 | A1 | 11/2005 | Anderson et al. | |
| 2007/0038206 | A1* | 2/2007 | Altshuler | A46B 15/0036 606/20 |
| 2008/0015557 | A1* | 1/2008 | Chan | A61B 18/203 606/17 |
| 2009/0254068 | A1* | 10/2009 | Karni | A61B 18/20 606/9 |
| 2011/0160712 | A1* | 6/2011 | Tankovich | A61B 18/22 606/9 |
| 2012/0010684 | A1* | 1/2012 | Owens | A61N 5/0616 607/88 |
| 2013/0197473 | A1* | 8/2013 | McMillan | A61B 18/203 604/501 |
| 2013/0281877 | A1 | 10/2013 | Hsu et al. | |
| 2014/0121631 | A1 | 5/2014 | Bean et al. | |
| 2014/0128881 | A1 | 5/2014 | Tyc et al. | |
| 2016/0220834 | A1 | 8/2016 | Schwarz | |
| 2019/0262072 | A1* | 8/2019 | Sakamoto | A61N 1/0484 |
| 2019/0374791 | A1* | 12/2019 | Tagliaferri | A61B 18/203 |
| 2020/0383728 | A1 | 12/2020 | Hofvander | |

FOREIGN PATENT DOCUMENTS

| | | |
|---|---|---|
| RU | 130846 U1 | 8/2013 |
| RU | 137201 U1 | 2/2014 |
| RU | 2635477 C2 | 11/2017 |
| WO | 2014135176 A1 | 9/2014 |
| WO | 2018076011 A1 | 4/2018 |
| WO | 2019234507 A1 | 12/2019 |

* cited by examiner

PHOTO-THERMAL TARGETED TREATMENT SYSTEM WITH INTEGRATED PRE-CONDITIONING, AND AUTOMATIC TRIGGERING OF PHOTO-THERMAL TARGETED TREATMENT VIA MEASUREMENT OF SKIN SURFACE TEMPERATURE AND ASSOCIATED METHODS

FIELD OF THE INVENTION

The present invention relates to photo-thermal targeted treatment and, more specifically, systems and methods for photo-induced thermal treatment targeting specific chromophores, or targets containing specific chromophores, embedded in a medium.

BACKGROUND OF THE INVENTION

Targets, such as chromophores and objects that contain chromophores, that are embedded in a medium can be thermally damaged by heating the target with a light source, such as a laser. For example, sebaceous glands that contain sebum that are embedded in the dermis can be thermally damaged by heating the sebum with a laser, until the sebum itself, or the sebaceous gland containing the sebum, is damaged. However, the application of enough thermal energy to damage the target can also be damaging to the surrounding dermis and the overlying epidermis, thus leading to epidermis and dermis damage as well as pain to the patient.

Previous approaches to prevent epidermis and dermis damage, as well as patient pain, include:
1. Pre-cooling the epidermis, then applying the photo-thermal treatment; and
2. Pre-cool the epidermis, also pre-condition (i.e., pre-heat) the epidermis and dermis in a preheating protocol, then apply a photo-thermal treatment in a distinct treatment protocol. In certain instances, the preheating protocol and the treatment protocol are performed by the same laser, although the two protocols involve different laser settings and application protocols, thus leading to further complexity in the treatment protocol and equipment.

SUMMARY OF THE INVENTION

In accordance with the embodiments described herein, a photo-thermal targeted treatment system for damaging a target embedded in a medium includes a controller and a photo-thermal treatment unit including a light source. The controller is configured for administering a treatment protocol and the treatment protocol is administered using the light source at a preset power setting and a preset pulse timing setting.

In another embodiment, the treatment protocol includes a pre-conditioning procedure for preheating the medium and the target and a photo-thermal treatment procedure. The pre-conditioning procedure and the photo-thermal treatment procedure are both administered using the light source, without changing the preset power setting and the preset pulse timing setting between the pre-conditioning procedure and the photo-thermal treatment procedure. In a further embodiment, the pre-conditioning procedure takes a longer duration of time than the photo-thermal procedure.

In still another embodiment, the system includes a cooling unit, and the treatment protocol further includes a cooling procedure prior to and during the treatment protocol. In yet another embodiment, for both the pre-conditioning procedure and the photo-thermal treatment procedure, the light source is set to emit a series of light pulses at a preset power level, preset pulse length, and preset pulse interval.

In yet another embodiment, the pre-conditioning procedure and the photo-thermal treatment procedure include the application of the light pulses in a scanned fashion over a preset area. In an exemplary embodiment, the preset area is a 2-by-2 matrix of 5 millimeter-by-5 millimeter treatment blocks.

In a further embodiment, during the pre-conditioning procedure and the photo-thermal treatment procedure, the temperature in the medium is less than a threshold for denaturation and damage of the medium, and the target is heated to a temperature greater than a damage threshold for the target. In an exemplary embodiment, the temperature of the medium (e.g., epidermis) is less than 55° C., and the target is heated to a temperature greater than 55° C. In another embodiment, the temperature of the medium is adjusted according to the location of the treatment area on the patient.

In another embodiment, a method for using a photo-thermal targeted treatment system for damaging a target embedded in a medium is disclosed. The system includes a light source. The method includes defining a set of parameters for a series of light pulses to be generated by the light source, the set of parameters including a preset power level, preset pulse length, a preset pulse interval, and a number of light pulses. The method also includes generating the series of light pulses, in accordance with the set of parameters as defined, and administering the series of light pulses to the medium.

In yet another embodiment, the method further includes cooling the medium while administering the treatment protocol. Further, in another embodiment, applying the series of light pulses includes defining the preset area as a matrix of treatment blocks of 2-by-1 and larger. In an exemplary embodiment, applying the series of light pulses includes defining the preset area as a 2-by-2 matrix of 5 millimeter by 5 millimeter treatment blocks.

In a further embodiment, administering the series of light pulses includes applying the series of light pulses such that a temperature of the medium is less than a threshold for denaturation and damage of the medium, and the target is heated to a temperature greater than a damage threshold for the target. In an exemplary embodiment, administering the series of light pulses includes raising a temperature of the medium (e.g., epidermis) to less than 55° C., while heating the target to a temperature greater than 55° C.

In accordance with the embodiments described herein, a method for automatically initiating a treatment protocol using a photo-thermal targeted treatment system is described. The method includes administering a cooling mechanism at the treatment location, monitoring a skin surface temperature at the treatment location, and when the skin surface temperature reaches a preset threshold, automatically initiating the treatment protocol.

In a further embodiment, the treatment protocol is initiated without any manual input by a user.

In accordance with another embodiment, a method for automatically terminating a treatment protocol using a photo-thermal targeted treatment system is described. The method includes, during administration of the treatment protocol at a treatment area, monitoring a skin surface temperature at the treatment location, and when the skin surface temperature reaches a preset threshold, automatically terminating the treatment protocol.

In accordance with a further embodiment, the treatment protocol is terminated without any manual input by a user.

Additional modifications and various to the contemplated embodiments are described hereinafter.

DETAILED DESCRIPTION OF EMBODIMENTS OF THE INVENTION

Embodiments of the present invention are described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Figure 1:
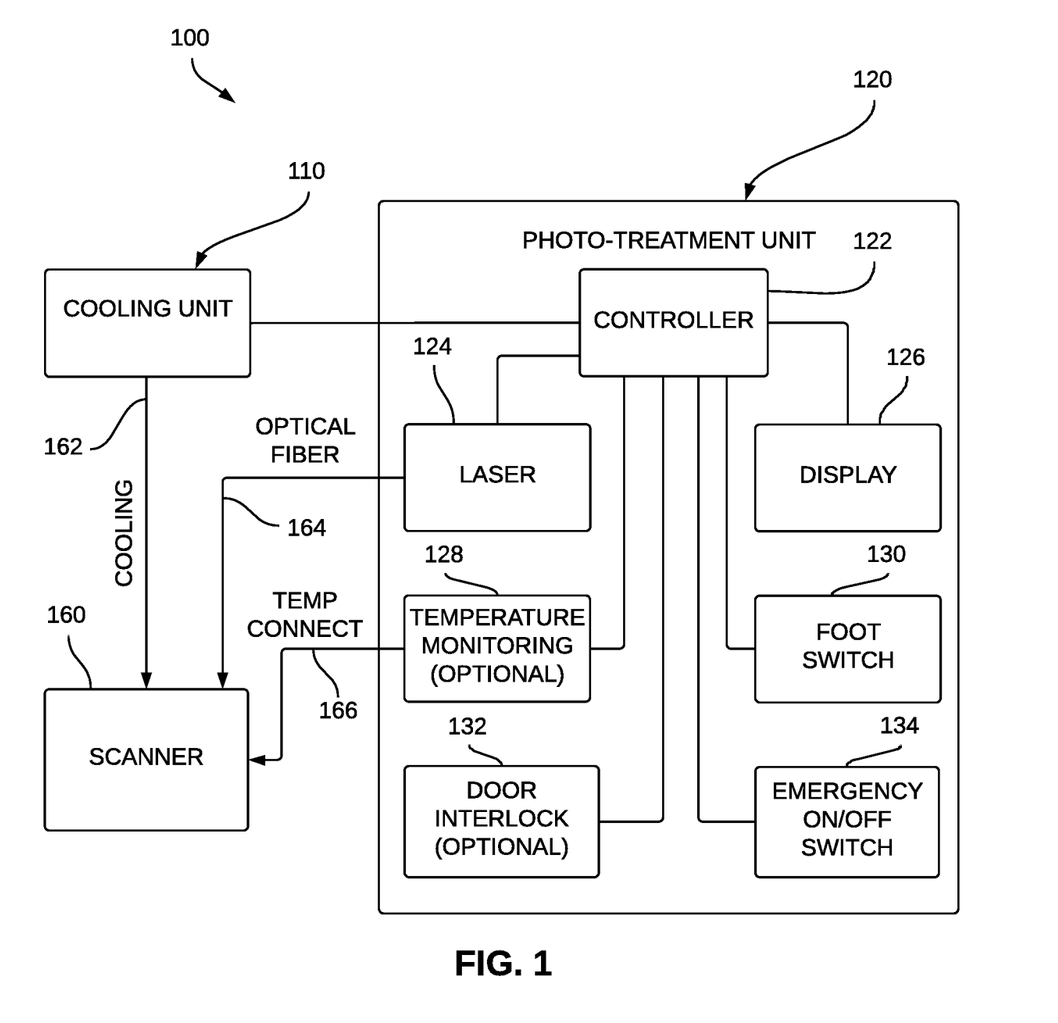
FIG. 1 illustrates an exemplary photothermal targeted treatment system, in accordance with an embodiment.

FIG. 1 shows an exemplary photo-thermal targeted treatment system for damaging a target, such as specific chromophores, or objects containing chromophores, embedded in a medium, and heating the target to a sufficiently high temperature so as to damage the target without damaging the surrounding medium. The system can be used, for example, for photo-thermal ablation of sebaceous glands, which contain sebum as the chromophore, in a targeted fashion, while sparing the epidermis and dermis surrounding the target sebaceous glands.

Still referring to FIG. 1, a photo-thermal targeted treatment system 100 includes a cooling unit 110 and a photo-treatment unit 120. Cooling unit 110 provides a cooling mechanism for a cooling effect, such as by contact or by direct air cooling, to treatment area, namely the outer skin layer area overlying the target sebaceous gland. Cooling unit 110 is connected with a controller 122 within photo-treatment unit 120. It is noted that, while controller 122 is shown to be contained within photo-treatment unit 120 in FIG. 1, it is possible for the controller to be located outside of both cooling unit 110 and photo treatment unit 122, or even within cooling unit 110.

Controller 122 further controls other components within photo-treatment unit 120, such as a laser 124, a display 126, a temperature monitoring unit 128, a foot switch 130, a door interlock 132, and an emergency on/off switch. Laser 124 provides the laser power for the photo-treatment protocol, and controller 122 regulates the specific settings for the laser, such as the output power and pulse time settings. Laser 124 can be a single laser or a combination of two or more lasers. If there more than one laser is used, the laser outputs are combined optically to function as one more powerful laser. Display 126 can include information such as the operating conditions of cooling unit 110, laser 124, and other system status. Temperature monitoring unit 128 is used to monitor the temperature of the skin surface in the treatment area, for example, and the measured skin surface temperature at the treatment area is used by controller 122 to adjust the photo-treatment protocol. Controller 122 also interfaces with footswitch 130 for remotely turning on or off laser 124 and/or cooling unit 110. Additionally, door interlock 132 can be used as an additional safety measure such that, when the door to the treatment room is ajar, door interlock 132 detects the condition and instructs controller 122 to not allow photo-treatment unit 120, or at least laser 124, to operate. Furthermore, emergency on/off switch 134 can be provided to quickly shut down photo-thermal targeted treatment system 100 in case of an emergency. In another modification, additional photodiodes or other sensors can be added to monitor the power level of the energy emitted from laser 124.

Continuing to refer to FIG. 1, photo-thermal targeted treatment system 100 further includes a hand-held scanner 160, which is the portion of the device held by the hand of the user in applying the treatment protocol to the patient. Scanner 160 can be formed, for example, in a gun-like or stick-like shape for ease of handling by the user. Scanner 160 is connected with cooling unit 110 via a cooling connection 162, such that the cooling protocol can be applied using scanner 160. Additionally, the output from laser 124 is connected with scanner 160 via an optical fiber delivery 164, such that the photo-treatment protocol can be applied using scanner 160. Optionally, scanner 160 is connected via a temperature connection 166 to temperature monitoring unit 128, so as to feedback the skin temperature at the treatment area, for example, to controller 122.

In the exemplary embodiment illustrated in FIG. 1, photo-treatment unit 120 of photo-thermal targeted treatment system 100 provides the light energy at a single setting that is used for both pre-conditioning of the treatment area as well as the photo-treatment of the target sebaceous gland. That is, rather than sequentially providing the application of light energy optimized for pre-conditioning, followed by a different light application optimized for photo-treatment, photo-treatment unit 120 provides the light energy used for both pre-conditioning and photo-treatment in a single, continuous application protocol without changing the light energy settings. This integrated protocol saves time and complexity in applying the photo-treatment.

Figure 2:
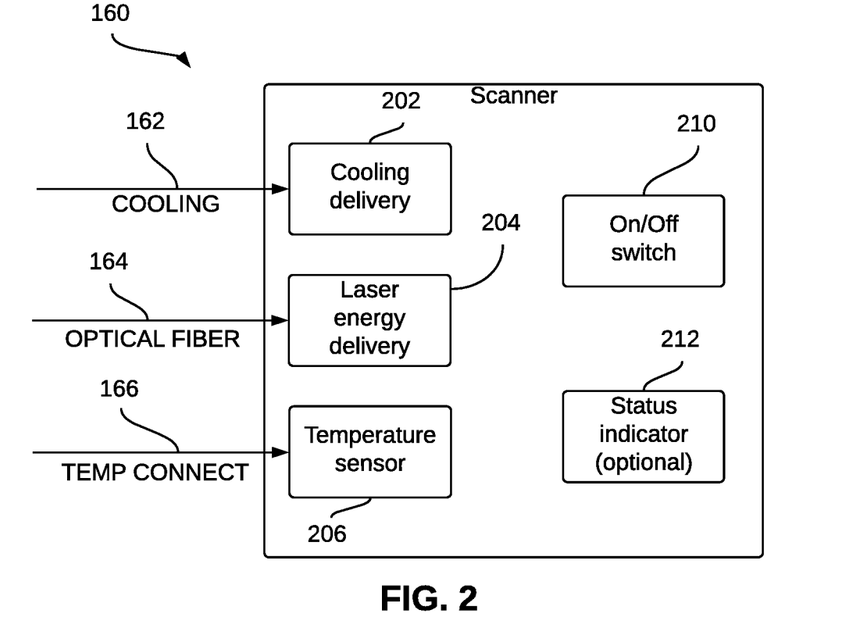
FIG. 2 illustrates an exemplary scanner arrangement for use with the photothermal targeting treatment system, in accordance with an embodiment.

FIG. 2 shows further details of scanner 160, in accordance with an embodiment. Cooling connection 162 is connected with a cooling delivery unit 202, which is configured to deliver the cooling mechanism (e.g., a cold air stream) to the treatment area. Optical fiber delivery 164, from laser 124, is connected with a laser energy delivery unit 204, which includes optical components for delivering light energy for the photo-thermal treatment protocol to the treatment area. Finally, temperature connection 166 is connected with a temperature sensor 206, which measures the temperature at the treatment area for feedback to controller 122. Additionally, scanner 160 includes an on/off switch 210 (such as a trigger switch to turn on/off laser 124) and, optionally, a status indicator 212, which indicates the operational status of scanner 160, such as if the laser is being operated. While scanner 160 is schematically shown as a box in FIG. 2, the actual shape is configured for ease of use. For example, scanner 160 can be shaped as a nozzle with a handle, a handgun shape, or another suitable shape for ease of aiming and control by the user.

In an exemplary method in accordance with an embodiment, a cooling protocol is applied to the overall treatment area. The cooling protocol can include, for example, the application of a cold airstream across the treatment area for a prescribed time period, such as 10 seconds. Following cooling, the cooling mechanism (e.g., cold airstream) remains active and a photo-treatment protocol is applied to the treatment area. In one embodiment, pulses of a square, "flat-top" beam is used in combination with a scanner apparatus to sequentially apply a laser pulse to segments within the treatment area. In accordance with an embodiment, the photo-treatment protocol includes the application of a set number of light pulses onto each of the segments in the treatment area, with the laser pulses being sequentially applied to the different segments. In another embodiment, the laser pulses are applied to the segments in a random order.

Figure 3:
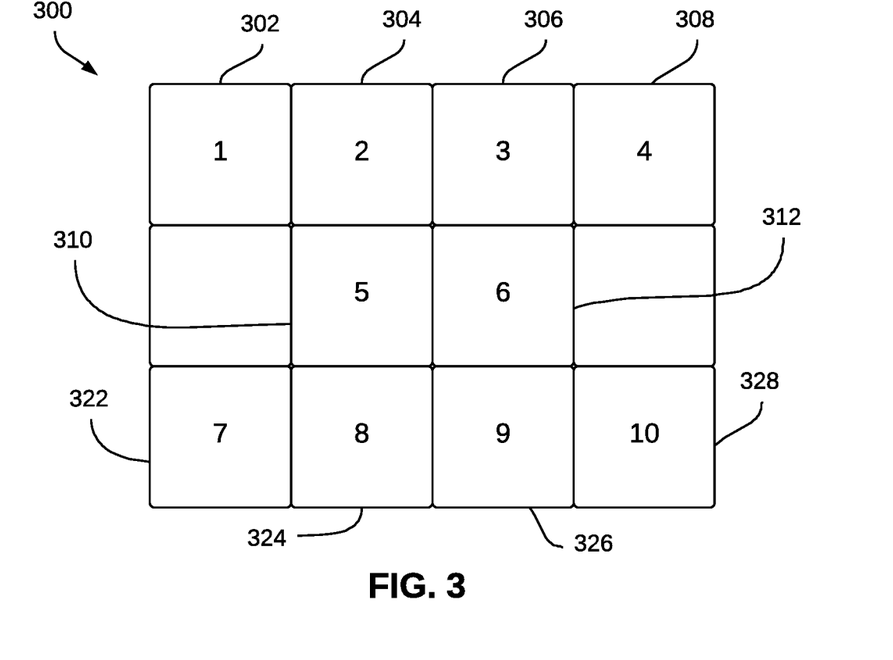
FIG. 3 illustrates an exemplary treatment matrix arrangement, in accordance with an embodiment.

In an exemplary usage scenario, the full treatment area overlying the sebaceous glands to be treated is cooled. A virtual grid configuration is overlaid over the treatment area as shown in FIG. 3. An exemplary grid configuration 300 includes twelve blocks, arranged in a 3×4 matrix. Many other grid configurations, such as a 1×1, 2×1, 2×2, etc., are possible. In the example shown, a treatment area is defined as a two-by-two block including blocks 310, 312, 324, and 326 (numbered 5, 6, 8, and 9, respectively).

In an exemplary method in accordance with an embodiment, a cooling protocol is applied to the overall treatment area (i.e., blocks 310, 312, 324, and 326) in grid configuration 300. The cooling protocol can include, for example, the application of a cold airstream across the treatment area for a prescribed time period, such as 10 seconds. Following cooling, the cooling mechanism (e.g., cold airstream) remains active and a pre-conditioning and photo-treatment protocol is applied to the treatment area. In one embodiment, pulses of a square, "flat-top" beam is used in combination with a scanner apparatus to sequentially apply a laser pulse to blocks 310, 312, 324, and 326. In accordance with an embodiment, the integrated pre-conditioning/photo-treatment protocol includes the application of a set number of light pulses onto each of the blocks in the treatment area, with the blocks being pulsed sequentially. In another embodiment, the blocks are pulsed in a random order.

Figure 4:
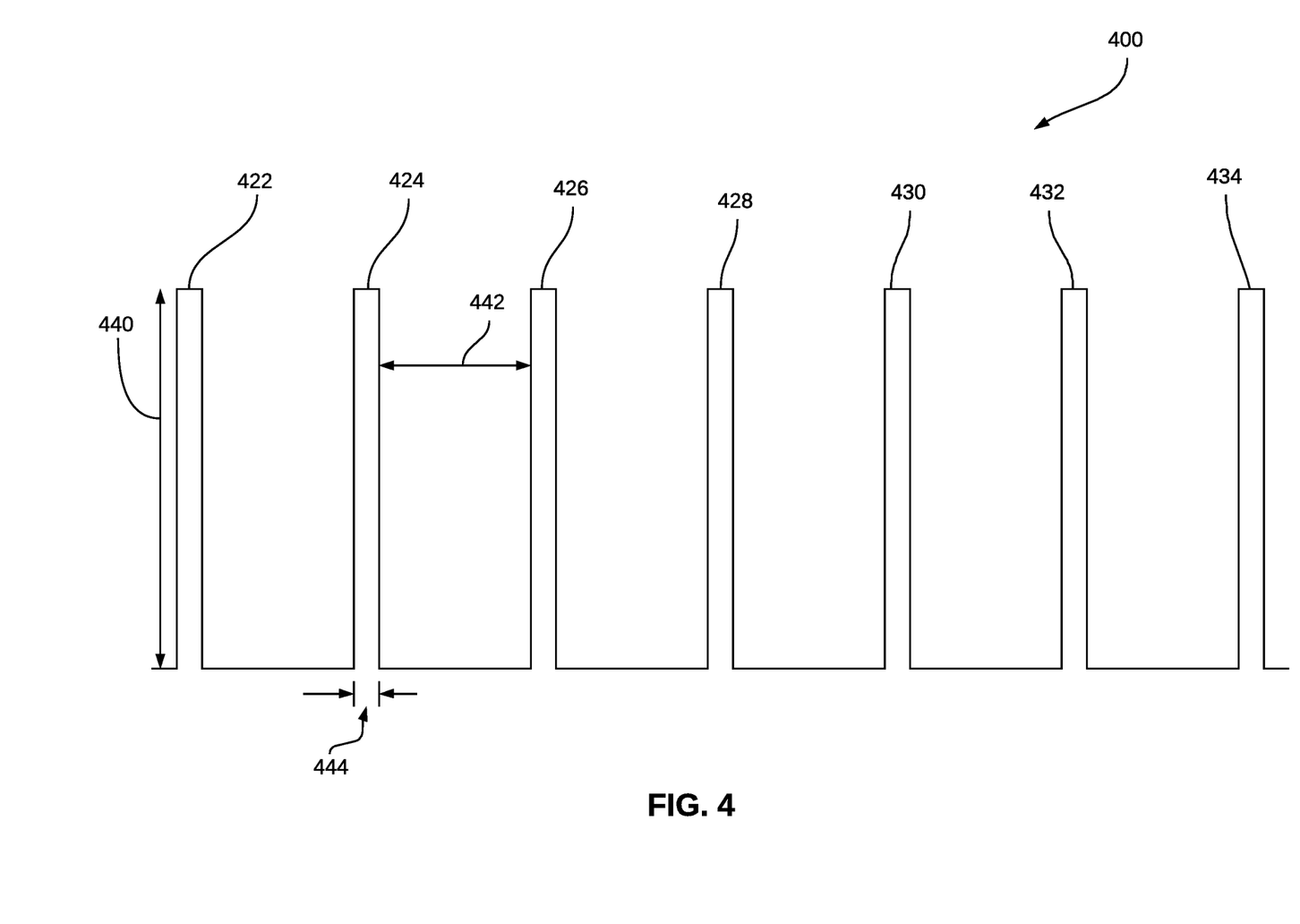
FIG. 4 shows a schematic of an exemplary set of light pulses suitable for use with a treatment protocol or an integrated pre-conditioning/photo-treatment protocol, in accordance with an embodiment.

An example of a set of pulses suitable for a treatment protocol or an integrated pre-conditioning/photo-treatment protocol is illustrated in FIG. 4, in accordance with an embodiment. A sequence 400 includes light pulses 422, 424, 426, 428, 430, 432, and 434 that are applied at one of the blocks within the treatment area. In one embodiment, all of the seven light pulses are of equal power, and are separated by a uniform pulse separation (represented by a double-headed arrow 442), and have the same pulse duration (represented by a gap 444). In an example, pulse duration 444 is 150 milliseconds, and the pulse separation is 2 seconds. The 2 second pulse separation is intended to allow the epidermis and dermis in the block to cool down so as to prevent damage thereto. During the pulse separation time period, the laser can be scanned over to a different block within the treatment area so as to increase the laser use efficiency. It is noted that FIG. 4 is not drawn to scale. Other configuration of the laser pulses are also possible, such as gradually increasing the power over multiple pulses, or varying the laser pulse parameters (e.g., pulse duration, pulse separation, and/or peak power) over multiple pulses. It is recognized that there are a variety of other pulse trains that will achieve the same average energy deposited in the skin tissue, while still maintaining short pulse durations.

Figure 5:
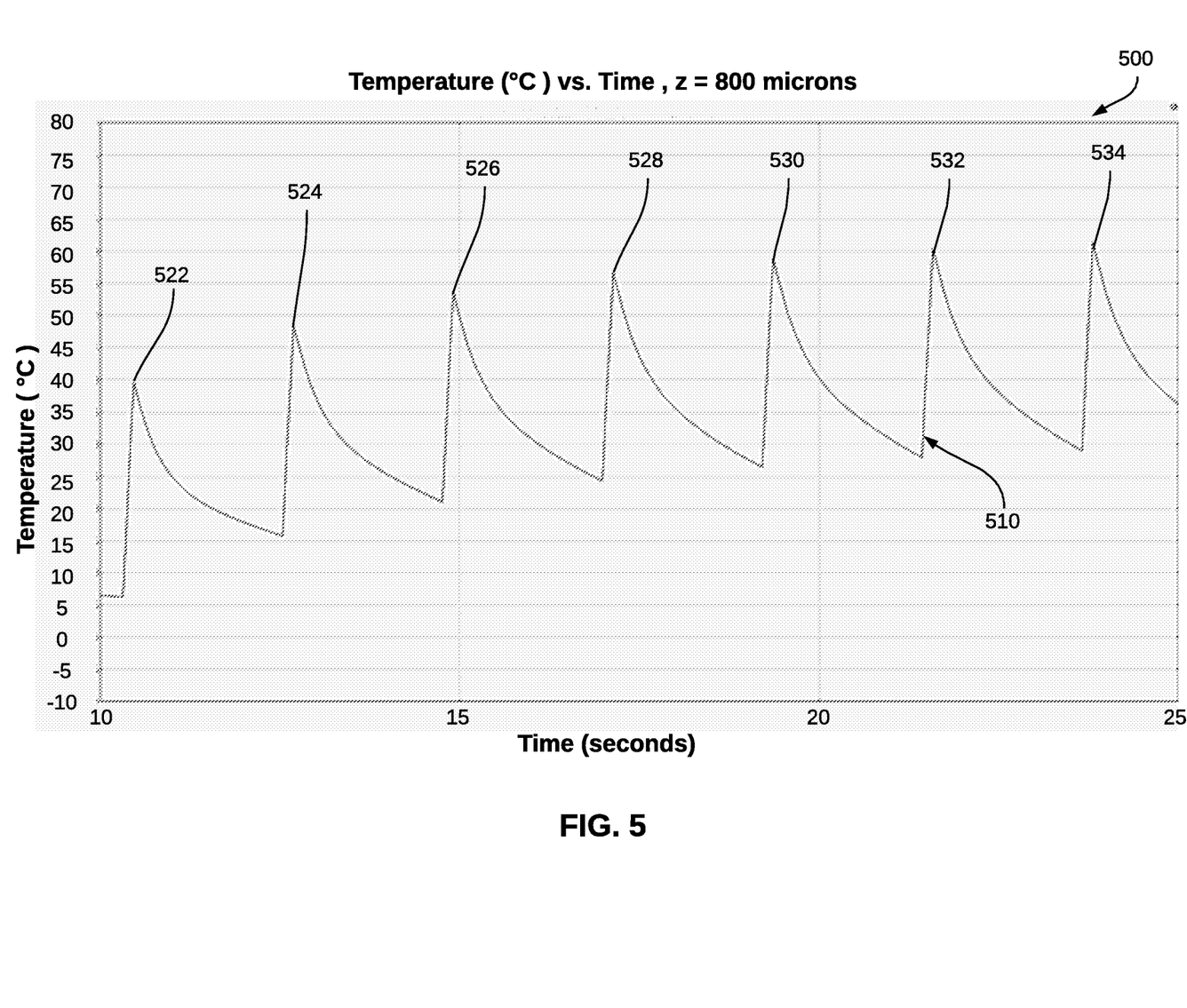
FIG. 5 shows the estimated temperature at the target sebaceous gland as a function of time as the treatment photo pulses are applied thereto, in accordance with an embodiment.

FIG. 5 shows the estimated temperature at the skin surface at the treatment area as light pulses, such as those shown in FIG. 4, are applied thereto, in accordance with an embodiment. In the example shown in FIG. 5, the treatment area had been cooled by direct air cooling for 7 seconds, then light pulses from a 1726 nm wavelength laser at 22 watts power and 150 milliseconds in duration were applied with a period of 2 seconds, while the cooling remains on. In this particular example, the direct-air cooling used for the cooling and during the treatment protocol, delivers a high-speed column of air, cooled to −22° C., resulting in a heat transfer coefficient between the skin and the air of roughly 350 W/m^2 K.

The beam size is 4.9 mm square, in an embodiment. The exact beam size can be adjusted, using for example collimation optics, depending on the size of the treatment area, power profile of the laser, the location of the treatment area of the body, and other factors. Furthermore, the average laser power per area should be in balance with the heat extraction achieved by the cooling system. The resulting changes in the measured skin surface temperature are shown in a graph 500, where a peak 522 corresponds to the application light pulse 422 as shown in FIG. 4, and similarly for peaks 424, 426, 428, and 430.

The pulse duration should be short enough to enable a rapid rise in the temperature at the target, e.g., the sebaceous gland, as long pulse durations can allow diffusion to soften the temperature peak. It is recognized that there are a variety of other pulse trains that will achieve the same average energy deposited in the skin tissue, while still maintaining short pulse durations. In example shown in FIG. 5, the average power per spot is 22 W*0.15 s/2 s=1.65 W. The same average power per spot can be achieved, for instance, by pulsing at 33 watts for 100 ms with a pulse separation of 2 s, or by pulsing at 25.1 W for 125 ms with a pulse separation of 1.9 s. Furthermore, the average laser power per area should be in balance with the heat extraction achieved by the cooling system.

Continuing to refer to FIGS. 4 and 5, it can be seen that light pulses 422, 424, 426, and 428 result in essentially a pre-conditioning effect, as the temperature at the target rises from approximately 40° C. at peak 522 up to nearly 57° C. at peak 528. Consequently, pulse 434 results in a peak 534 at a temperature of approximately 61° C., which is above the damage threshold for the target containing the chromophore (i.e., the sebaceous gland containing sebum). In this way, simply by repeatedly applying light pulses with the same characteristics, the pre-conditioning and photo-treatment protocols are effectively integrated, thus eliminating the need for a separate pre-conditioning system and protocol that is different from the photo-treatment system and protocol.

It is also noted that the number of light pulses applied for pre-conditioning purposes is slightly larger than the number of light pulses that effect the photo-treatment. This characteristic is reversed from existing photo-thermal targeted treatment systems in that existing systems have tried to minimize the amount of time taken for pre-conditioning due to the difficulties in balancing the cooling and pre-conditioning effects for pain management during the treatment. The system and methods as described herein eliminate the concern of minimizing the pre-conditioning time, as the same light pulse settings for pre-conditioning are used for the photo-treatment.

The successful photo-thermal treatment of specific targets with decreased patient discomfort may include: 1) Epidermis sparing, namely the peak temperature value at the epidermis is less than around 55° C.; 2) Dermis sparing, namely avoiding overheating the dermis by balancing the average power of the treatment pulses with the heat extraction of the cooling system; and 3) Selective heating of the target target, such as a peak temperature greater than 55° C. for sebaceous gland treatment. Additionally, during the cooling phase, over-cooling the treatment area should be avoided, in order to prevent cold damage (e.g., frostbite) to the epidermis.

It is noted that the number of pulses applied during the photo-thermal treatment protocol can be in a range between 2 pulses and up to approximately 100 pulses depending on such variables as effectiveness of the cooling, laser power, pulse width, and pulse frequency.

Alternatively, a raster scanning process can be used to scan a continuous wave laser beam across the treatment area, rather than applying a laser pulse to a particular block, then moving the laser to another block for application of another laser pulse. In this case with raster scanning, the temperature rise in the target, e.g., the sebaceous gland, can be calculated as a convolution of the size of the sebaceous gland and the speed of the beam.

It is known in the literature that tissue parameters, such as the thickness of the epidermis and dermis, vary among individuals, according to factors such as age, gender, ethnicity, pH, oil content, and hydration as well as between different skin locations. For example, the forehead has different tissue properties than the back, even for the same individual, thus necessitating different treatment parameter settings for the different treatment locations. While existing treatment protocols have been based on a "one treatment fits all" type of an approach, such variations in tissue properties in determining the specific treatment protocol can significantly influence the effectiveness of the laser-based treatment of acne. Additionally, there may be variations in, for instance, the exact laser power, spot size, and cooling capacity between specific laser systems due to manufacturing variability and operating conditions. Mitigating treatment variations that can be caused by variations in the laser power output of a specific machine, as well as variations in treatment conditions, such as ambient humidity and temperature, helps to achieve more uniform treatment results. In other words, reducing variability during photo-thermal treatments enhances safety and increases efficacy.

Figure 6:
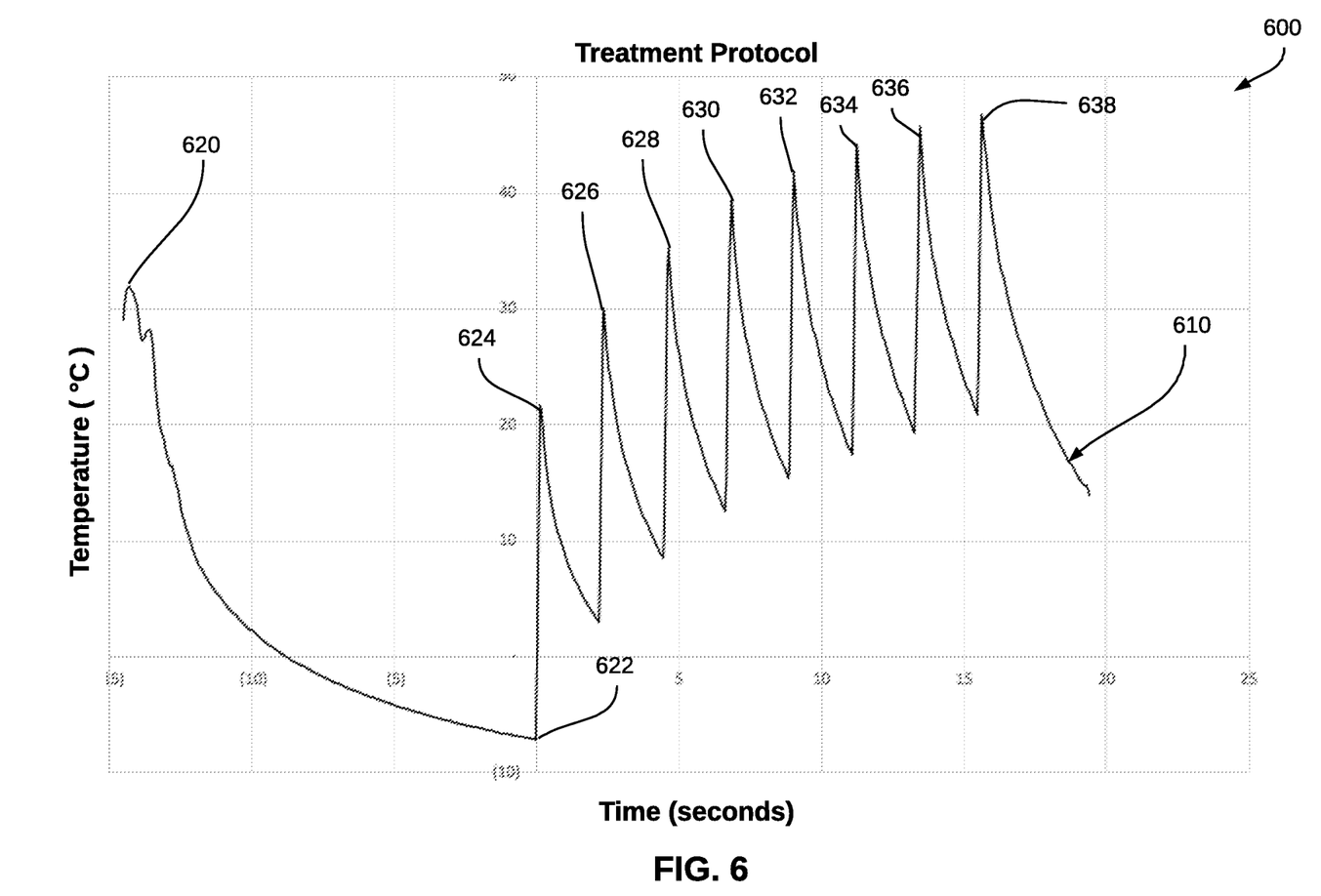
FIG. 6 shows the measured temperature at the skin surface as a function of time during a treatment protocol, in accordance with an embodiment.

In one aspect, any variation in the skin surface temperature at the start of a photo-thermal treatment protocol affects the thermal transfer of the laser pulse energy to the target. For instance, in FIG. 6, whereas the treatment protocol as shown had cooled the skin surface to approximately −7° C. when the first laser pulse is applied, if the skin had been cooler or warmer, then the initial peak (i.e., peak 624) would have reached a different temperature, thus affecting the overall temperature rise of during subsequent laser pulse application.

For existing photo-thermal treatment systems, this variation in the skin surface temperature at the start of the photo-thermal treatment protocol is inevitable, as the cooling procedure includes the application of a cooling means (e.g., cold air or a chilled surface) for a preset amount of time. As an example, the user is directed by the photo-thermal treatment system to apply a stream of cold air onto the treatment area for a certain number of seconds, then the user is prompted to initiate the photo-thermal treatment protocol including the application of the laser pulses. However, this process does not consider the potential variations in the photo-thermal treatment system performance as well as the thermal coefficients of the skin surface in the treatment area, thus inevitably leading to variability in the treatment efficacy.

In an embodiment, a method for performing a treatment includes monitoring the skin surface temperature during the cooling and automatically triggering the pre-conditioning and photo-thermal treatment protocol when a threshold skin surface temperature is reached, and without user intervention.

This cooling monitoring and automatic treatment protocol triggering can be performed by incorporating temperature measurements using, for example, a commercial, off-the-shelf, low-cost sensor that can be built into the scanner (e.g., see temperature sensor 206 of FIG. 2) that is held by the medical professional to apply the treatment to the patient, or by using a separate, commercial off-the-shelf single or multi-pixel thermal measurement devices. The monitoring process can be performed on a highly localized level, thus adjusting the timing of the initialization of the treatment protocol on the fly. In this way, the treatment protocol can be specified to provide the appropriate cooling effect for patient comfort, while staying above the epidermis and dermis damage threshold temperature in the cooling phase.

Figure 7:
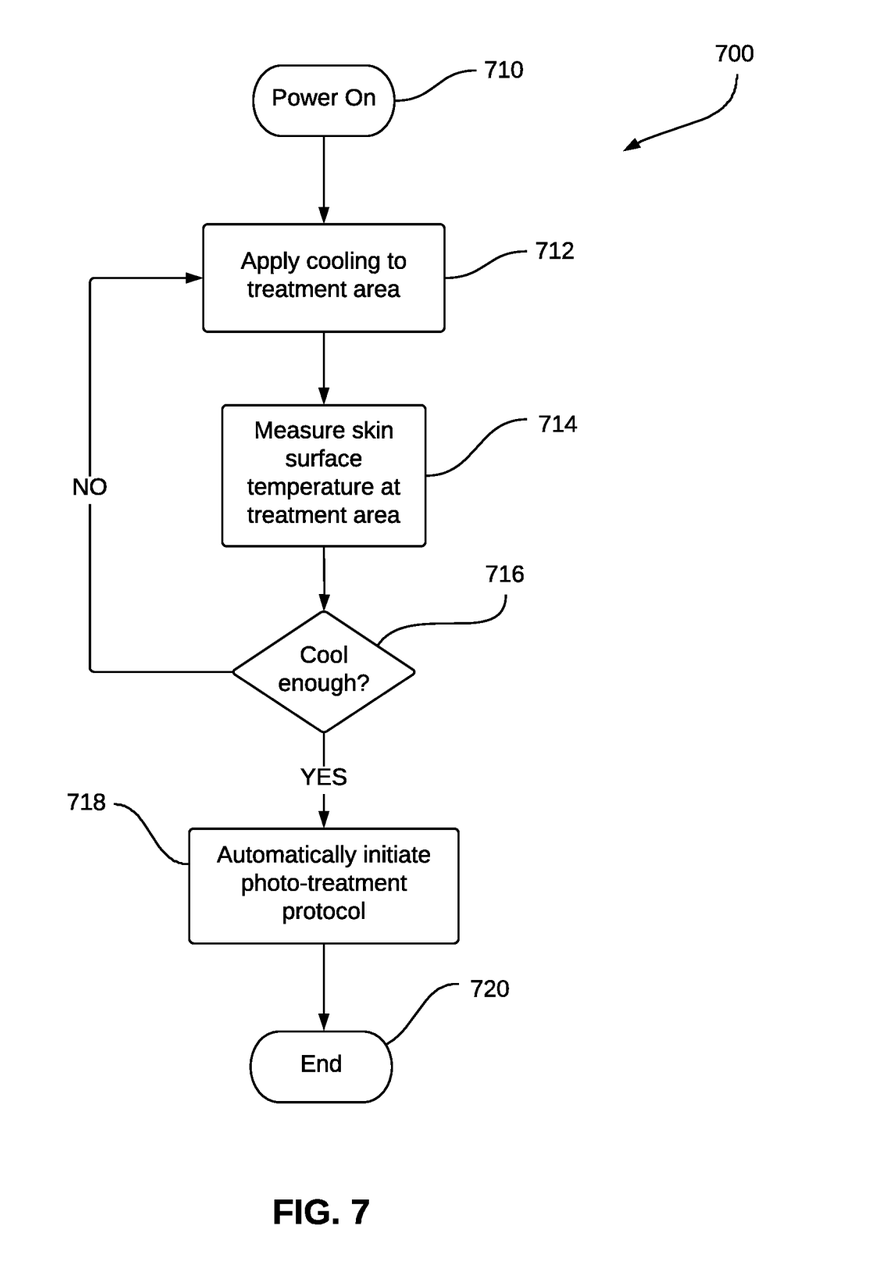
FIG. 7 shows a flow chart illustrating an exemplary process for analyzing the measured skin surface temperature during the cooling portion of the treatment protocol, then initiating the treatment protocol accordingly.

Turning to FIG. 7, a flow chart illustrating an exemplary process for cooling monitoring and automatic initiation of the photo-treatment protocol, in accordance with an embodiment. As shown in FIG. 7, an automatic treatment initiation process 700 begins by powering on the system in an initialization step 710, then applying a cooling mechanism to a treatment area in a step 712. The cooling mechanism can be, for example, a cold air stream. The skin surface temperature at the treatment area is then measured in a step 714. The temperature measurement can be performed, for example, using a low speed infrared camera or similar apparatus. Then a determination is made in a decision 716 whether the measured skin surface temperature is cool enough (e.g., −5° C. or another preset temperature setting) to begin application of the treatment protocol. If the answer to decision 716 is NO, then the process returns to step 712, at which the cooling mechanism is continued to be applied to the treatment area.

If the answer to decision 716 is YES, then automatic treatment initiation process 700 proceeds to automatically initiate the treatment protocol, without intervention from the user, in a step 718. The automatic treatment initiation process is ended in a step 720.

Optionally, for safety reasons and control purposes, the current skin surface temperature can be compared to stored thresholds value adapted to different control parameters. The monitoring of the skin surface temperature at the treatment area can be continued throughout the treatment protocol as well as after the conclusion of the laser pulse application such that, if the cooling mechanism is continued to be applied to the treatment area, the cooling mechanism application can be stopped once the measured epidermis temperature has reached, for instance, the room temperature or another preset post-treatment temperature setting.

Figure 8:
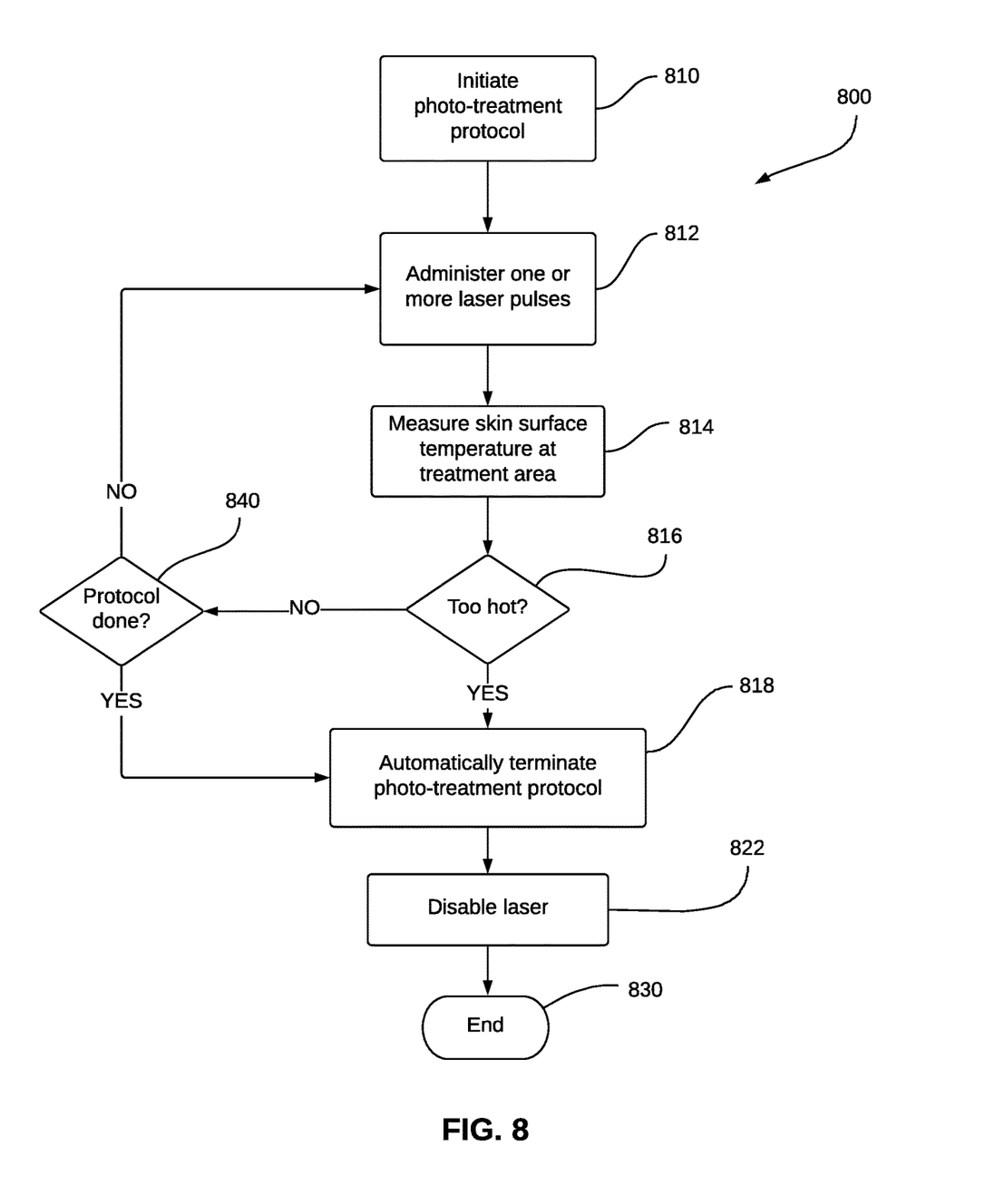
FIG. 8 shows a flow chart illustrating an exemplary process for continuing to analyze the measured skin surface temperature during the treatment protocol, then terminating the treatment protocol accordingly.

An optional, additional process of automatically terminating the treatment protocol without human intervention is illustrated in FIG. 8. As shown in FIG. 8, an automatic treatment termination process 800 begins with a step 810 to initiate a photo-treatment protocol. Step 810 can be, for example, photo-treatment initiation step 718 of FIG. 7. Alternatively, automatic treatment termination process 800 is applicable for use with any photo-treatment protocol regardless of the manner of treatment protocol initiation.

Continuing to refer to FIG. 8, automatic treatment termination process 800 proceeds to a step 812 to administer a set of laser pulses to a treatment area. During or immediately following the application of the set of laser pulses, the skin surface temperature is measured at the treatment area in a step 814. A decision 816 is then made to determine whether the measured skin surface temperature is higher than a preset threshold temperature (i.e., too hot) or not. If the answer to decision 816 is YES, then automatic treatment termination process proceeds to a step 818 to automatically terminate the photo-treatment protocol without further involvement of the user. The laser is disabled in a step 822, and the process is ended in a step 830. If the answer to decision 816 is NO, then the treatment protocol continues to a decision 840 to determine whether the treatment protocol has been completed. If the answer to decision 840 is NO, then the process returns to step 812 to continue administration of additional laser pulses to the treatment area. For example, if the treatment protocol is defined as the application of eight laser pulses at a specific treatment area and only seven or fewer laser pulses have been applied to that point, then additional laser pulses are triggered as long as the skin surface temperature is below the damage threshold. If the answer to decision 840 is YES, then the process proceeds to steps 818, 822, and 830 to wind down the treatment protocol without further user intervention.

Still referring to FIG. 8, the cooling mechanism can continue to optionally be applied to the treatment area through steps 812, 814, 816, 818, and/or 840 in order to mitigate potential overheating of the treatment area. In an example, for a larger treatment area (e.g., a 2-by-2 matrix of 5 millimeter-by-5 millimeter treatment blocks), a set number of laser pulses (ranging from one to eight, for example) is applied to each treatment block in turn. For instance, step 812 to administer the laser pulses includes the application of one laser pulse at a first treatment block, in an embodiment.

The skin surface temperature is measured in step 814 and, if the measured skin surface temperature is below the preset threshold and the photo-treatment protocol includes the application of additional pulses, then the process returns to step 812 to apply additional laser pulses to the treatment area. Then, in an example, a second laser pulse is applied to the first treatment block, or the aim of the laser is moved to a second treatment block to apply a laser pulse thereto. The aim of the laser can be moved after each laser pulse, or consecutive laser pulses can be applied to a single treatment block before aiming the laser to a second treatment block. For instance, if there is a time delay of up to two seconds between laser pulse applications, then a temperature reading of the treatment area can be made during the time delay and a decision made regarding whether or not to apply additional laser pulses. In an embodiment, treatment parameters such as the laser power, laser beam size, treatment area dimensions, and the number of laser pulses to be applied per treatment block, are predefined by a user, while the automatic treatment termination process allows real time and ad hoc adjustment of the treatment protocol to reduce the chance of potential damage to the treatment area, even without user intervention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. For example, lasers with other wavelengths, such as around 1210 nm, can be used. An important aspect of the embodiments described herein is the increased safety for the patient by making the treatment protocol initiation and/or termination automatic such that potential tissue damage due to operator error is reduced.

Accordingly, many different embodiments stem from the above description and the drawings. It will be understood that it would be unduly repetitious and obfuscating to literally describe and illustrate every combination and subcombination of these embodiments. As such, the present specification, including the drawings, shall be construed to constitute a complete written description of all combinations and subcombinations of the embodiments described herein, and of the manner and process of making and using them, and shall support claims to any such combination or subcombination.

The present disclosure includes the following clauses, which are part of the present disclosure.

Clause 1. A photo-thermal targeted treatment system for damaging a target embedded in a medium, the system including a controller; and a photo-thermal treatment unit including a light source, wherein the controller is configured for administering a treatment protocol, and wherein the treatment protocol is administered using the light source at a preset power setting and a preset pulse timing setting.

Clause 2. The system of Clause 1, wherein the treatment protocol includes a pre-conditioning procedure for preheating the medium, and a photo-thermal treatment procedure, wherein the pre-conditioning procedure and the photo-thermal treatment procedure are both administered using the light source, without changing the preset power setting and the preset pulse timing setting between the pre-conditioning procedure and the photo-thermal treatment procedure, and wherein the pre-conditioning procedure takes a longer duration of time than the photo-thermal procedure.

Clause 3. The system of Clause 2, further including a cooling unit, wherein the treatment protocol further includes a cooling procedure for cooling the medium while administering the treatment protocol.

Clause 4. The system of Clause 3, wherein, for both the pre-conditioning procedure and the photo-thermal treatment procedure, the light source is set to emit a series of light pulses at a preset power level, preset pulse length, and preset pulse interval.

Clause 5. The system of Clause 4, wherein the preset power level is in a range of 10 watts to 50 watts per pulse.

Clause 6. The system of Clause 4, wherein the preset pulse length is in a range of 25 milliseconds to 200 milliseconds per pulse.

Clause 7. The system of Clause 4, wherein the preset pulse interval is in a range of 0.5 seconds to 2.5 seconds.

Clause 8. The system of Clause 4, wherein the pre-conditioning procedure and the photo-thermal treatment procedure include application of the light pulses in a scanned fashion over a preset area.

Clause 9. The system of Clause 8, wherein the preset area is a matrix of treatment blocks of 2-by-1 and larger.

Clause 10. The system of Clause 8, wherein the preset area is a 2-by-2 matrix of 5 millimeter-by-5 millimeter treatment blocks.

Clause 11. The system of Clause 4, wherein, during the pre-conditioning procedure and the photo-thermal treatment procedure, a temperature of the medium is less than a damage threshold for the medium, and the target is heated to a temperature greater than a damage threshold for the target.

Clause 12. The system of Clause 11, wherein, during the pre-conditioning procedure and the photo-thermal treatment procedure, a temperature of the medium is less than 55° C., and the target is heated to a temperature greater than 55° C.

Clause 13. The system of Clause 11, further including a temperature monitor for measuring a temperature of the medium as the series of light pulses are being applied to the medium.

Clause 14. A method for using a photo-thermal targeted treatment system for damaging a target embedded in a medium, the system including a light source, the method including: 1) defining a set of parameters for a series of light pulses to be generated by the light source, the set of parameters including a preset power level, preset pulse length, a preset pulse interval, and a number of light pulses; 2) generating the series of light pulses, in accordance with the set of parameters as defined; and 3) administering the series of light pulses to the medium.

Clause 15. The method of Clause 14, further including, before administering the series of light pulses to the medium, cooling the medium for cooling the medium before and while administering the series of light pulses.

Clause 16. The method of Clause 15, wherein applying the series of light pulses includes defining the preset area as a matrix of treatment blocks of 2-by-1 and larger.

Clause 17. The method of Clause 16, wherein applying the series of light pulses includes defining the preset area as a 2-by-2 matrix of 5 millimeter-by-5 millimeter treatment blocks.

Clause 18. The method of Clause 14, wherein administering the series of light pulses includes applying the series of light pulses such that a temperature of the medium is less than a damage threshold for the medium, and the target is heated to a temperature greater than a damage threshold for the target.

Clause 19. The method of Clause 14, wherein administering the series of light pulses includes raising a temperature of the medium to less than 55° C., while heating the target to a temperature greater than 55° C.

Clause 20. The method of Clause 14, further including monitoring a temperature of the medium as the series of light pulses are administered to the medium.

Clause 21. A method for automatically initiating a treatment protocol using a photo-thermal targeted treatment system, the method including administering a cooling mechanism at a treatment location; monitoring a skin surface temperature at the treatment location; and when the skin surface temperature reaches a preset threshold, automatically initiating the treatment protocol.

Clause 22. The method of Clause 21, wherein automatically initiating the treatment protocol is performed without any manual input by a user.

Clause 23. A method for automatically terminating a treatment protocol using a photo-thermal targeted treatment system, the method including, during administration of the treatment protocol at a treatment area, monitoring a skin surface temperature at the treatment location, and when the skin surface temperature reaches a preset threshold, automatically terminating the treatment protocol.

Clause 24. The method of Clause 23, wherein automatically terminating the treatment protocol is performed without any manual input by a user.

In the specification, there have been disclosed embodiments of the invention and, although specific terms are employed, they are used in a generic and descriptive sense only and not for purposes of limitation. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of embodiments of the present invention and is not to be construed as limited to the specific embodiments disclosed, and that modifications to the disclosed embodiments, as well as other embodiments, are intended to be included within the scope of the appended claims. The invention is defined solely by the following claims, and the full scope of the equivalents thereof.

What is claimed is:

1. A photo-thermal targeted treatment system for damaging a target embedded in a medium, the system including
   a controller;
   a photo-thermal treatment unit including a laser; and
   a cooling unit;
   wherein the controller is configured for administering a treatment protocol,
   wherein the treatment protocol is administered using the laser at a preset power setting and a preset pulse timing setting;
   wherein the treatment protocol includes
      a pre-conditioning procedure for preheating the target and the medium, and a photo-thermal treatment procedure, wherein the pre-conditioning procedure and the photo-thermal treatment procedure are both administered using the laser, without changing the preset power setting and the preset pulse timing setting between the pre-conditioning procedure and the photo-thermal treatment procedure, and
      a cooling procedure for cooling the medium while administering both the pre-conditioning procedure and the photo-thermal treatment procedure of the treatment protocol,
   wherein, while administering the treatment protocol, the laser is set to emit a series of light pulses at a preset power level, preset pulse length, and preset interval between consecutive pulses, and wherein each pulse of said series of light pulses comprise a flat top pulse; and
   wherein the treatment protocol includes application of the light pulses in a scanned fashion over a preset area.

2. The system of claim 1, wherein the preset power level is in a range of 10 watts to 50 watts per pulse.

3. The system of claim 1, wherein the preset pulse length is in a range of 25 milliseconds to 200 milliseconds per pulse.

4. The system of claim 1, wherein the preset interval between consecutive pulses is in a range of 0.5 seconds to 2.5 seconds.

5. The system of claim 1, wherein the preset area includes a matrix of treatment blocks of 2-by-1 or larger.

6. The system of claim 1, wherein the preset area includes a 2-by-2 matrix of 4 to 6 millimeter-by-4 to 6 millimeter treatment blocks.

7. The system of claim 1, wherein, while administering the treatment protocol, a temperature of the medium is less than a damage threshold for the medium, and the target is heated to a temperature greater than a damage threshold for the target.

8. The system of claim 7, wherein, while administering the treatment protocol, the temperature of the medium is less than 55° C., and the target is heated to a temperature greater than 55° C.

9. The system of claim 7, further including a temperature monitor for measuring the temperature of the medium.

10. The system of claim 1, further including a hand-held scanner connected to the cooling unit and an output of the laser, the scanner being adapted to apply both the cooling procedure and the photo-thermal treatment procedure.

11. The system of claim 1, wherein the application of the light pulses comprises moving the laser after each light pulse.

12. The system of claim 1, wherein the application of the light pulses comprises consecutive light pulses being applied to a first treatment block before moving the laser to a second treatment block.

13. The system of claim 1, wherein the application of the light pulses comprises a time delay of up to two seconds between light pulses; and
   wherein the treatment protocol further includes measuring a temperature of the medium during the time delay, and wherein the controller is further configured to determine whether or not to apply a subsequent light pulse based on the temperature.

14. A method for using a photo-thermal targeted treatment system for damaging a target embedded in a medium, the system including a laser, the method including:
   1) Defining a set of parameters for a series of light pulses to be generated by the laser, the set of parameters including a preset power level, preset pulse length, a preset interval between consecutive pulses, and a number of light pulses;
   2) Generating the series of light pulses, in accordance with the set of parameters as defined, wherein each pulse of said series of light pulses comprise a flat top pulse; and
   3) Administering the series of light pulses to the medium in a scanned fashion over a preset area according to a treatment protocol; wherein the treatment protocol comprises administering a pre-conditioning procedure for pre-heating the target and the medium, and a photo-thermal treatment procedure, wherein the pre-conditioning procedure and the photo-thermal treatment procedure are both administered using the laser, without changing the preset power level and the preset interval between consecutive pulses; and cooling the medium with a cooling unit while administering the treatment protocol.

15. The method of claim 14, wherein administering the series of light pulses includes applying the series of light pulses such that a temperature of the medium is less than a damage threshold for the medium, and the target is heated to a temperature greater than a damage threshold for the target.

16. The method of claim 14, wherein administering the series of light pulses includes raising a temperature of the medium to less than 55° C., while heating the target to a temperature greater than 55° C.

17. The method of claim 14, further including monitoring a temperature of the medium as the series of light pulses are administered to the medium.

18. A method for automatically initiating a treatment protocol using a photo-thermal targeted treatment system, the method comprising:

administering a cooling mechanism at a treatment location;

monitoring a skin surface temperature at the treatment location; and when the skin surface temperature reaches a preset threshold, automatically initiating the treatment protocol, wherein the treatment protocol comprises using a laser to emit a series of light pulses at a preset power level, preset pulse length, and preset interval between consecutive pulses in a scanned fashion over a preset area, wherein each pulse of said series of light pulses comprise a flat top pulse, and administering a pre-conditioning procedure for pre-heating the treatment location and administering a photo-thermal treatment procedure, wherein the pre-conditioning procedure and the photo-thermal treatment procedure are both administered using the laser, without changing the preset power setting and the preset pulse timing setting between the pre-conditioning procedure and the photo-thermal treatment procedure.

19. The method of claim 18, wherein automatically initiating the photo-thermal treatment protocol in response to the skin surface temperature reaching the preset threshold is performed without a manual input by a user.

20. A method for automatically terminating a photo-thermal treatment protocol using a photo-thermal targeted treatment system, the method comprising:

defining a set of parameters for a series of light pulses to be generated by a laser, the set of parameters including a preset power level, preset pulse length, a preset interval between consecutive pulses, and a number of light pulses;

administering a pre-conditioning procedure for preheating a treatment area by generating a series of light pulses to the treatment area;

administering the photo-thermal treatment protocol to the treatment area by generating a second series of light pulses to the treatment area in a scanned fashion over a preset area, wherein each pulse of said second series of light pulses comprise a flat top pulse, and wherein the pre-conditioning procedure and the photo-thermal treatment procedure are both administered using the laser, without changing the preset power level and the preset interval between consecutive pulses;

cooling the treatment area during the photo-thermal treatment protocol using a cooling unit;

during administration of the treatment protocol at the treatment area, monitoring a skin surface temperature at the treatment area; and when the skin surface temperature reaches a preset threshold, automatically terminating the photo-thermal treatment protocol.

21. The method of claim 20, wherein automatically terminating the treatment protocol is performed without a manual input by a user.

* * * * *